(12) United States Patent
Alini et al.

(10) Patent No.: US 8,557,584 B2
(45) Date of Patent: Oct. 15, 2013

(54) PREPARING A HOMOGENOUS POPULATION OF STEM CELLS COMMITTED TO DIFFERENTIATED TO A SPECIFIC CELL TYPE

(75) Inventors: Mauro Alini, Davos Platz (CH); Martin Stoddart, Sargans (CH)

(73) Assignee: Ao-Forschungsinstitut Davos, Davos (CH)

( * ) Notice: Subject to any disclaimer, the term of this patent is extended or adjusted under 35 U.S.C. 154(b) by 849 days.

(21) Appl. No.: 12/089,494

(22) PCT Filed: Aug. 11, 2006

(86) PCT No.: PCT/CH2006/000425
§ 371 (c)(1),
(2), (4) Date: Apr. 7, 2008

(87) PCT Pub. No.: WO2008/017171
PCT Pub. Date: Feb. 14, 2008

(65) Prior Publication Data
US 2009/0304652 A1    Dec. 10, 2009

(51) Int. Cl.
*C12N 15/00* (2006.01)
*C12N 5/00* (2006.01)

(52) U.S. Cl.
USPC .................. 435/455; 435/325; 435/377

(58) Field of Classification Search
None
See application file for complete search history.

(56) References Cited

PUBLICATIONS

Kashiwakura et al., Isolation of bone marrow stromal cell-derived smooth muscle cells by a human SM22alpha promoter: in vitro differentiation of putative smooth muscle progenitor cells of bone marrow, Circulation 107(16):2078-81, 2003.*
Li et al., Mechanical load modulates chondrogenesis of human mesenchymal stem cells through the TGF-beta pathway, J Cell Mol Med.14(6A):1338-46, 2010.*
Kupcsik et al., Improving chondrogenesis: potential and limitations of SOX9 gene transfer and mechanical stimulation for cartilage tissue engineering, Tissue Eng Part A. 16(6):1845-55, 2010.*
Kornberg,The molecular basis of eukaryotic transcription (Nobel Lecture), Angew Chem Int Ed Engl. 46(37):6956-65, 2007.*
Valdimarsdottir et al., Functions of the TGFbeta superfamily in human embryonic stem cells. APMIS, 113(11-12):773-89, 2005.*
Ptashne et al. Transcriptional activation by recruitment, Nature 386 (6625): 569-77, 1997.*
Ng et al., The transcriptional and signalling networks of pluripotency, Nat Cell Biol. 13(5):490-6, 2011.*
Roche, Enrique et al.; "The use of gating technology in bioengineering insulin-secreting cells from embryonic stem cells"; Cytotechnolgoy; vol. 41, No. 2-3; 2003; pp. 145-151; XP002402056.
Benveniste, Ronald J. et al.; "Embryonic stem cell-derived astrocytes expressing drug-inducible transgenes: differentiation and transplantion into the mouse brain"; Journal of Neurosurgery; vol. 103, No. 1; Jul. 2005; pp. 115-123; XP002402057.
Mueller M. et al.; "Selection of ventricular-like cardiomyocytes from ES cells in vitro"; FASEB Journal, Fed.of American Soc. for Experimental Biology; Bethesada, Maryland; vol. 14, No. 15; Dec. 2000; pp. 2540-2458; XP002180458.
Keyoung, H. Michael et al.; "High-yield selection and extraction of two promoter-defined phenotypes of neural stem cells from the fetal human brain"; Nature Biotechnology; vol. 19, No. 9; Sep. 2001; pp. 1087-0156; pp. 843-850; XP002402058.
Sambrook et al., Molecular Cloning: A Laboratory Manual (Third Edition), vol. 1, Chapter 13: Mutagenesis, pp. 13.1 to 13.10; Coldspring Harbor Laboratories Press (United States—2001).
Sambrook et al., Molecular Cloning: a Laboratory Manual (Third Edition), vol. 1, Chapter 15: Expression of Cloned Genes in *Escherichia coli*, pp. 15.4 to 15.6; Coldspring Harbor Laboratories Press (United States—2001).
Ausubel et al., Short Protocols in Molecular Biology, vol. 1, Chapter 3: Enyzmatic Manipulation of DNA and RNA, pp. 3-39 to 3-43; Wiley & Sons (New York—2002).
Ausubel et al., Short Protocols in Molecular Biology, vol. 1, Chapter 8: Mutagenisis of Cloned DNA, pp. 8-16, 8-18, 8-20 and 8-21; Wiley & Sons (New York—2002).
Ausubel et al., Short Protocols in Molecular Biology, vol. 1, Chapter 10: Analysis of Proteins, pp. 10-86 and 10-88; Wiley & Sons (New York—2002).
Elder et al., Effect of Compressive Loading on Chondrocyte Differentiation in Agarose Cultures of Chick Limb-Bud Cells, Journal of Orthopedic Research, 18:78-86, The Journal of Bone and Joint surgery, Inc., (2000) Orthopaedic Research Society.

* cited by examiner

*Primary Examiner* — Deborah Crouch
(74) *Attorney, Agent, or Firm* — Rankin, Hill & Clark LLP (57) ABSTRACT

The stem cell (1) includes a cellular DNA (2) comprising a plurality of sequences coding different genes and promoters allowing DNA-protein-interactions, at least one protein molecule (3) generated by means of a specific stimulus (12) and at least one DNA-molecule (6) artificially introduced into the stem cell (1).
The artificially introduced DNA-molecule (6) comprises at least one binding site sequence (30) being apt to interact with the protein molecule (3), at least one DNA-sequence (40) coding an indicator molecule (5) and at least one minimal promoter sequence (50), allowing the gene expression of said indicator molecule (5), whereby the stem cell further includes at least one indicator molecule (5) having properties allowing its identification and is produced by synthesis of the DNA-sequence (40) coding an indicator molecule (5) of the artificially introduced DNA-molecule (6).

5 Claims, 4 Drawing Sheets

| | Example 1 | Example 2 | Example 3 | Example 4 | Example 5 |
|---|---|---|---|---|---|
| Specific stimulus | Osteogenic Medium | Angiogenic Medium | Neurogenic Medium | Chondrogenic Medium | Myogenic Medium |
| Decisive additive | 10nM dexamethasone | 50 ng/ml VEGF | 5-10 mM β-Mercaptoethanol | 10 ng/ml TGF beta | 50 μM Hydrocortisone |
| Specific Transcription Factor protein | Runx2 | HOX9A | NRSF/REST | Sox9 | MyoD |
| Specific type of the stem cells | Osteoblast | Endothelial | Nerve cell | Chondrocyte | Myocyte |

Fig. 4

PREPARING A HOMOGENOUS POPULATION OF STEM CELLS COMMITTED TO DIFFERENTIATED TO A SPECIFIC CELL TYPE

BACKGROUND OF INVENTION

1. Field of Invention

The present invention relates to a modified stem cell, a homogeneous population of modified stem cells committed to differentiate to the same specific phenotype of stem cells, to a method for producing single identifiable stem cells committed to differentiate to a specific phenotype and to a method for the identification and selection of embryonic, foetal or adult stem cells that are committed to differentiate into a specific type of cell for obtaining homogeneous populations of stem cells.

2. Description of Related Art

Currently, stem cells in a sample of different cells can only be isolated as a heterogeneous population of cells, i.e. as a pool of many cells with the potential to differentiate into different types of cells (for example, hematopoietic and non-hematopoietic cells from bone marrow aspirate, umbilical cord blood or blood samples). Some "rough" selection or enrichment can be done by using antibodies that recognize cell surface antigens present on some of these heterogeneous cell populations (for example CD34 or CD133). Once these antibodies have reacted with the cells, these cells (defined as CD34 or CD133 positive cells) can be isolated by FACS (the antibody has a fluorescence marker) or by magnetic selection (using the MACS technology from Miltenyi Biotec). However, because of the fact that these antigens (which react with the CD34 or CD133 antibodies) are present on different cells, such procedures result also in heterogeneous stem cell populations although a partial enrichment (or selection) will have been done following these procedures.

BRIEF SUMMARY OF THE INVENTION

On this point, the invention intends to provide remedial measures. The invention is based on the objective of providing a stem cell allowing the modification of the stem cells in a population of stem cells in order to identify stem cells committed to differentiate to the same specific phenotype and select the identified stem cells to a homogeneous population.

The invention solves the posed problem with a stem cell that includes:
- a cellular DNA comprising a plurality of sequences coding different genes and promoters allowing DNA-protein-interactions;
- at least one protein molecule generated by means of a specific stimulus;
- at least one DNA-molecule artificially introduced into the stem cell whereby the artificially introduced DNA-molecule comprises:
  - (I) at least one binding site sequence being apt to interact with the protein molecule;
  - (II) at least one DNA-sequence coding an indicator molecule; and
  - (III) at least one minimal promoter sequence, allowing the gene expression of said indicator molecule and
- at least one indicator molecule produced by synthesis of the DNA-sequence coding an indicator molecule of the artificially introduced DNA-molecule;
whereby
  - the indicator molecule has properties allowing its identification; and wherein
  - the protein molecule is a specific transcription factor protein which increases the expression of the gene associated with the change to a specific phenotype,
which can be identified and separated from the other stem cells. The invention also solves the posed problem with a method for obtaining an essentially homogenous population of stem cells that comprises the following steps:
- collecting a stem cells sample comprising stem cells each including cellular DNA which comprises a plurality of sequences coding different genes and promoters allowing DNA-protein-interactions;
- artificially introducing of at least one DNA-molecule into a plurality of cells of the stem cells sample producing a modified stem cell sample whereby the introduced DNA-molecule comprises:
  - (I) at least one binding site sequence being apt to interact with a protein molecule;
  - (II) at least one DNA-sequence coding an indicator molecule having properties allowing its identification; and
  - (III) at least one minimal promoter sequence, allowing the gene expression of the indicator molecule;
- adding a culture medium to the modified stem cell sample;
- applying a specific stimulus to the modified stem cells sample, whereby the specific stimulus generates the protein molecule in at least one cell of the modified stem cells sample;
- identification of stem cells comprising protein molecules by means of identification of the presence of the indicator molecule by means of its properties in the stem cell;
- whereby said indicator molecule has been produced by synthesis of the DNA-sequence being initiated by means of the interaction between the protein molecule and the binding site sequence of the introduced DNA-molecule;
- selection of the identified stem cells by means of the properties of the indicator molecule to an essentially homogeneous population;
- identification of daughter stem cells containing the introduced DNA-molecule after the cell division by means of identification of the presence of the indicator molecule by means of its properties; and
- selection and removal of the identified daughter stem cells from the population.

One advantage achieved by the invention is essentially to be seen in the fact that thanks to the stem cell according to the invention a population of the stem cells being committed to differentiate to the same type can be obtained in vitro and can be used for targeted application in vivo.

All scientific terms used herein shall be understood to have the following meanings:
"introduce" as used herein refers to transduction or transfection of a foreign genetic material (DNA) into a cell and identifies a viral transduction and/or a non-viral transfection/transformation;
"cellular DNA" refers to the original stem cell DNA, i.e. what the cell naturally contains;
"transcription factor protein" is a protein that regulates the activation of transcription in the cells. Transcription factor proteins localize to regions of promoter and enhancer sequence elements either through direct binding to DNA or through binding other DNA-bound proteins. The function of a transcription factor protein is to bind specific DNA sequences and modulate changes in gene expression (also called transcription) as a result of its binding;

"specific DNA-protein-interaction" refers to the DNA-protein interaction being dependent on a nucleotide sequence;

"specific sequence" refers to a nucleotide sequence allowing interactions with a "specific" protein only i.e. with a protein being destined to interact with this nucleotide sequence;

"Cellular differentiation" refers to a process by which cells become a specific type;

"Transcription" refers to a process by which RNA is synthesized using a DNA template, thereby transferring genetic information from the DNA to the RNA;

"Translation" refers to a process of transforming the information contained in the nucleotide sequences of an RNA to the corresponding amino acid sequence of a polypeptide as specified by the genetic code;

"Promoter" refers to the DNA sequence at which RNA polymerase binds to initiate the transcription; and "Reporter" refers to a plasmid or DNA construct which encodes an easily identifiable protein. It serves to demonstrate the presence of a particular DNA sequence or a particular DNA binding protein within a population of cells.

In a special embodiment of the invention, the protein molecule is a transcription factor protein increasing the expression of the gene associated with the change to a specific phenotype. Often a family of genes is controlled by a single factor called a transcription factor protein. This protein binds specific DNA sequences and increases the expression of the gene associated with the change to a specific phenotype. As a transcription factor protein is an early expressed gene, and only expressed in cells which will become a specific phenotype associated with this specific transcription factor protein, (i.e. each transcription factor protein is present in stem cells which have been stimulated to become a phenotype specific to the transcription factor protein only). The protein molecule is also apt to initiate the transcription of the DNA-sequence coding an indicator molecule of the artificially introduced DNA-molecule by means of interaction with the binding site sequence of the artificially introduced DNA-molecule and so that the protein initiates synthesis of the indicator molecule.

In a further embodiment the binding site sequence in the artificially introduced DNA-molecule is positioned such that it drives the expression of the DNA-sequence coding an indicator molecule by way of the minimal promoter sequence.

In yet a further embodiment the minimal promoter sequence is arranged in the artificially introduced DNA-molecule between the binding site sequence and the DNA-sequence coding an indicator molecule.

The cell phenotype is dependant on the stimulus received by the non-committed stem cell. Once stimulated, the cell changes its phenotype by switching off certain genes while switching on other genes. Such stimulus might be a physical, chemical or biochemical stimulus. An example of a physical stimulus would be the use of mechanical load (compression and shear) of cells seeded into a scaffold during chondrocyte differentiation. An example of a chemical stimulus would be dexamethasone present is osteogenic medium. An example of a biochemical stimulus would be TGF beta in chondrogenic medium.

In a further embodiment the indicator molecule has properties allowing the selection and removal of the stem cell containing the indicator molecule from a stem cell sample. The properties of the indicator molecule allowing its identification and/or selection might be chemical, biochemical or physical properties.

In another embodiment the indicator molecule is a cell surface expressed protein, foreign to the native stem cell population, which presence in the stem cell is also identifiable.

In a further embodiment the indicator molecule has ferromagnetic properties. The term "ferromagnetism" is used therein for any material that could exhibit spontaneous magnetization: a net magnetic moment in the absence of an external magnetic field.

In another embodiment the DNA-sequence of the artificially introduced DNA-molecule is a sequence coding a green fluorescence protein (GFP), a protein from the jellyfish *Aequorea victoria* that fluoresces green when exposed to blue light. Color mutants obtained from the GFP gene, in particular the cyan fluorescent protein (CFP) and the yellow fluorescent protein (YFP) might also be used. As an alternative to fluorescence indicator molecules mentioned above, any indicator molecules which are non-toxic to the cells and can be introduced into the cells and emit any light/energy that can be detected by any signal detection device could be used.

When using a fluorescent indicator molecule, such as green fluorescent protein (GFP), the cells could be identified in monolayer using fluorescence microscopy or in a single cell suspension using fluorescent activated cell sorting (FACS).

When using a magnetic indicator molecule such as ferritin, the cells can be isolated using a magnetic capture system.

When using a cell surface expressed protein, foreign to the native stem cell population, the cells can be identified using fluorescently labeled antibodies directed against the introduced protein and isolated by FACS. Alternatively the cells can be isolated using a bead capture system such as DYNAL beads, whereby the antibody reacting against the novel epitope is first combined with a DYNAL bead and then the bead is used to capture the cells of interest.

The introduced DNA molecule has been introduced into the stem cell e.g. by means of a viral transduction or by means of a non-viral transfection. The introduced DNA-molecule is introduced to the stem cell but is not introduced into the original cellular DNA of the stem cell, so that the introduced DNA will not be replicated by the cell division and will be existent in only one of the daughter cells. The advantages of such embodiments can be seen in the fact that after the isolation and (multiple) cell division the stem cell comprising the introduced DNA-molecule can be isolated from the obtained stem cell population in order to obtain a stem cell population of unmodified stem cells.

In further embodiments the artificially introduced DNA-molecule comprises at least two DNA-sequences, each coding a different indicator molecule.

In one such embodiment of the artificially introduced DNA-molecule comprising at least two DNA-sequences, each coding a different indicator molecule, this DNA might comprise one binding site sequence being able to interact with the protein molecule, one minimal promoter sequence and two DNA-sequences each coding a different indicator molecule, whereby these DNA-sequences are linked to each other.

Figure 4:
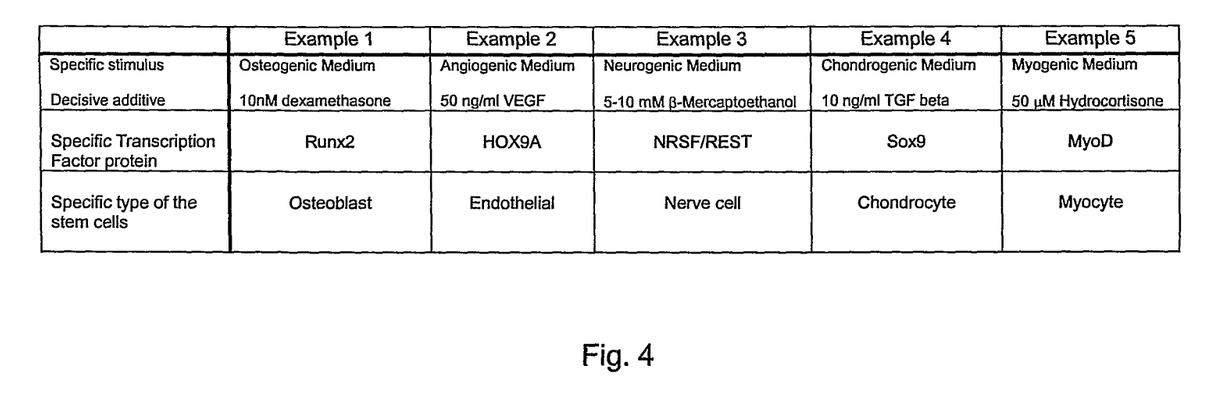
FIG. 4 shows a table describing the correlation between specific stimulus, decisive additive of the specific stimulus, specific transcription factor protein being expressed in the cells stimulated to become a specific type and specific phenotype of the stem cells.

In case the stem cell is committed to differentiate to a specific phenotype, which corresponds the protein molecule, which is able to interact with the binding site sequence of the artificially introduced DNA-molecule (the correlation between the specific phenotype and protein molecule is shown in FIG. 4), the protein molecule would be present in the cell and would interact with the binding site sequence of the artificially introduced DNA-sequences, so that two different indicator molecules coded by these DNA-sequences will be synthesized. The advantage of such an embodiment can be seen in the fact that the one of the indicator molecules is selectable in order to meet criteria of better identification possibilities and the other indicator molecule is selectable in order to meet criteria of better selection possibilities.

In a further embodiment the artificially introduced DNA-molecule comprises two sequences, each coding a different indicator molecule, this DNA might comprise two or more sequence blocks each comprising one binding site sequence being able to interact with the protein molecule, one minimal promoter sequence and one DNA-sequence coding an indicator molecule, whereby the two DNA-sequences code two different indicator molecules and both binding site sequences are able to interact with the same protein molecule. This embodiment allows also the possibility that one of the indicator molecules is selectable in order to meet criteria of better identification possibilities and the other indicator molecule is selectable in order to meet criteria of better selection possibilities.

In another embodiment the artificially introduced DNA-molecule comprising two sequences, each coding a different indicator molecule, this DNA comprises two or more sequence blocks each comprising one binding site sequence (UBS) being able to interact with the protein molecule, one minimal promoter sequence (MP) and one DNA-sequence coding an indicator molecule, whereby both DNA-sequences code two different indicator molecules and the binding site sequences are able to interact with two different protein molecules, whereby these different protein molecules correspond to two different phenotypes of cells. The advantage of such an embodiment can be seen in the fact that two different populations of stem cells comprising stem cells committed to differentiate to two different specific phenotypes of stem cells can be identified and isolated from a stem cell sample. These can later be mixed together if so wished.

For example the sequence blocks may be physically joined together on the same DNA molecule in the following order: UBS (e.g. for osteoblast)-MP-indicator molecule (green)-UBS (e.g. for chondrocyte)-MP-indicator molecule (blue).

In a further embodiment the number of such sequence blocks can be optionally increased, whereby each different indicator molecule coded by the DNA-sequence should correspond to one specific binding site sequence. The advantage of such an embodiment can be seen in the fact that only one DNA-molecule shall be artificially introduced into each cell of the obtained stem cell sample and that by the adequate number of such sequence blocks essentially all cells of the obtained stem cell sample can be isolated from the heterogeneous stem cell sample to a plurality of the homogeneous populations of stem cells committed to differentiate to the same specific phenotype of the stem cells.

In an another embodiment each stem cell comprises at least two introduced DNA-molecules each comprising a DNA-sequence coding an indicator molecule, whereby the DNA-sequences (40) of the introduced DNA-molecules are coding different indicator molecules. Additionally, the different indicator molecules might have different properties. Such embodiments allow the advantage of the combination of two indicator molecules having different properties allowing better identification and selection. This also allows for the concurrent selection of multiple cell types, as well as providing an investigative tool to investigate differentiation pathways.

The introduced DNA-molecule might also comprise
  a mutated minimal promoter sequence, in order to prevent non-specific transcription factor protein interaction with DNA, which would eliminate any minor expression caused by other transcription factor;
  at least one additional binding site sequence (A). The advantage of this embodiment can be seen in the fact that by adding the further identical sequence more transcription factors can interact with DNA-sequences, so that the gene expression might be additionally enhanced. This increases also the number of the indicator molecules and makes the desired cells easier to identify.

The genetically unmodified homogeneous population as well as the homogeneous population of stem cells containing partially genetically modified daughter stem cells as well as unmodified daughter stem cells is useable for tissue engineering purposes. The populations are applicable for all already known stem cells applications, and shows the advantage of a homogeneous population in contrary to the known prior art application.

Tissue Engineering of Bone can be achieved by seeded the isolated, unmodified stem cell population onto a biocompatible scaffold material and implanting the construct into the bone defect. The construct may or may not be subjected to a period of in vitro culture prior to implantation.

Alternatively in the case of muscle, the isolated and purified cell population may be directly injected into the defect allowing the cells to migrate to the point of injury and effect a repair.

An agent for the in vivo treatment of tissue diseases prepared by use of the homogeneous population of stem cells, committed to differentiate to the same specific phenotype of the stem cell might be administered in combination with further additives such as hormones, vitamins, growth factors, further proteins, further enzymes or a combination thereof.

In a further embodiment the stem cell is used for the identification of the presence of the protein molecule in said stem cell.

In a further embodiment the stem cell is used for the selection of the stem cell containing the protein molecule.

Another embodiment of the invention comprises an essentially homogeneous population of stem cells committed to differentiate to the same specific phenotype of the stem cells said population being obtainable by the following steps:
  A) collecting a stem cells sample comprising stem cells each including a cellular DNA which comprises a plurality of sequences coding different genes and promoters allowing DNA-protein-interactions;
  B) artificially introducing at least one DNA-molecule to a plurality of stem cells of the stem cells sample producing a modified stem cell sample;
  whereby the introduced DNA-molecule comprises
    at least one binding site sequence being apt to interact with a protein molecule;
    at least one DNA-sequence coding an indicator molecule having properties allowing the identification of said indicator molecule; and
    at least one minimal promoter sequence, allowing the gene expression of the indicator molecule;
  C) adding a culture medium to the modified stem cells sample;
  D) applying a specific stimulus to the modified stem cells sample, whereby the specific stimulus generates the protein molecule in at least one stem cell of the modified stem cells sample;
  E) identification of stem cells comprising protein molecules by means of identification of the presence of the indicator molecule by means of its properties in the stem cell;
  F) whereby said indicator molecule has been produced by synthesis of the DNA-sequence being initiated by means of the interaction between the protein molecule and the binding site sequence (A) of the introduced DNA-molecule; and G) selection of the identified stem cells by means of the properties of the indicator molecule to said essentially homogeneous population of stem cells.

Yet, another embodiment of the invention comprises an essentially homogeneous population of stem cells comprising stem cells committed to differentiate to the same specific phenotype of stem cells whereby each of the stem cells comprises:

A) a cellular DNA comprising a plurality of sequences coding different genes and promoters allowing DNA-protein-interactions;

B) at least one protein molecule generated by means of a specific stimulus; and

C) at least one DNA-molecule artificially introduced into the stem cell, whereby the introduced DNA-molecule comprises
  at least one binding site sequence being apt to interact with the protein molecule;
  at least one DNA-sequence coding an indicator molecule; and
  at least one minimal promoter sequence, allowing the gene expression of the indicator molecule
and D) at least one indicator molecule produced by synthesis of the DNA-sequence coding an indicator molecule of the introduced DNA-molecule; whereby E) the indicator molecule has properties for its identification.

According to one embodiment of the population the indicator molecule has properties allowing the selection of the stem cells containing said indicator molecule.

Again another embodiment of the invention comprises an essentially homogeneous unmodified population of stem cells, committed to differentiate to the same specific phenotype of the stem cells obtainable by the following steps:

A) collecting a stem cells sample comprising stem cells each including a cellular DNA which comprises a plurality of sequences coding different genes and promoters allowing DNA-protein-interactions;

B) artificially introducing at least one DNA-molecule to a plurality of stem cells of the stem cells sample producing a modified stem cell sample;

whereby the introduced DNA-molecule comprises
  at least one binding site sequence being apt to interact with a protein molecule;
  at least one DNA-sequence coding an indicator molecule having properties allowing the identification and selection of said indicator molecule; and
  at least one minimal promoter sequence, allowing the gene expression of the indicator molecule;

C) adding a culture medium to the modified stem cells sample;

D) applying a specific stimulus to the modified stem cells sample, whereby the specific stimulus generates the protein molecule in at least one stem cell of the modified stem cells sample;

E) identification of stem cells comprising protein molecules by means of identification of the presence of the indicator molecule by means of its properties in the stem cell, F) whereby said indicator molecule has been produced by synthesis of the DNA-sequence being initiated by means of the interaction between the protein molecule and the binding site sequence (A) of the introduced DNA-molecule;

G) selection of the identified stem cells by means of the properties of the indicator molecule to an essentially homogeneous population;

H) identification of daughter stem cells containing the artificially introduced DNA-molecule after the natural cell division by means of identification of the presence of the indicator molecule by means of its properties;

selection and removal of the identified daughter stem cells from the population, which has been obtained after said cell division for obtaining an essentially homogeneous unmodified population of stem cells, committed to differentiate to the same specific phenotype.

According to a further embodiment of that population the protein molecule is a transcription factor protein increasing the expression of the gene associated with the change to a specific phenotype.

According to another embodiment of the population the minimal promoter sequence is arranged in the artificially introduced DNA-molecule between the binding site sequence and the DNA-sequence coding an indicator molecule.

According to a further embodiment of the population the specific stimulus is a physical, biochemical or chemical stimulus.

According to yet another embodiment of the population the properties of the indicator molecule allowing the identification and/or the selection of said indicator molecule are chemical, biochemical or physical properties.

According to a further embodiment of the population the introduced DNA-molecule comprises at least two DNA-sequences, each coding a different indicator molecule.

According to still another embodiment of the population each stem cell of the population comprises at least two introduced DNA-molecules each comprising a DNA-sequence coding an indicator molecule, whereby the DNA-sequences of the introduced DNA-molecules are coding different indicator molecules.

According to another embodiment of the population the different indicator molecules have different properties.

According to a further embodiment of the population the introduced DNA molecule includes a sequence coding an indicator molecule having properties of a ferromagnetic molecule.

According to a further embodiment of the stem cell the introduced DNA molecule includes a sequence coding a cell surface expressed protein, foreign to the native stem cell population.

Another object of the invention is the use of the unmodified population for tissue engineering purposes.

A further object of the invention is the use of the population for the preparation of an agent for the in vivo treatment of tissue and blood diseases.

Still a further object of the invention is the use of the population for the preparation of an agent for the in vitro treatment of tissue and blood diseases, in particular for leukemia.

Still another object of the invention is the use of the population whereby the agent is to be administered in combination with further additives.

Yet another object of the invention is the use of the population whereby the additives are hormones, vitamins, growth factors, further proteins, further enzymes or a combination thereof.

A further embodiment of the method for obtaining an essentially homogeneous population of stem cells being committed to differentiate to the same specific phenotype comprises the following steps:
- A) collecting a stem cells sample comprising stem cells each including cellular DNA which comprises a plurality of sequences coding different genes and promoters allowing DNA-protein-interactions;
- B) artificially introducing of at least one DNA-molecule into a plurality of cells of the stem cells sample producing a modified stem cell sample,
  whereby the introduced DNA-molecule comprises
    at least one binding site sequence being apt to interact with a protein molecule;
    at least one DNA-sequence coding an indicator molecule having properties allowing its identification; and
    at least one minimal promoter sequence, allowing the gene expression of the indicator molecule;
- C) adding a culture medium to the modified stem cell sample;
- D) applying a specific stimulus to the modified stem cells sample, whereby the specific stimulus generates the protein molecule in at least one cell of the modified stem cells sample;
- E) identification of stem cells comprising protein molecules by means of identification of the presence of the indicator molecule by means of its properties in the stem cell;
- F) whereby said indicator molecule has been produced by synthesis of the DNA-sequence being initiated by means of the interaction between the protein molecule and the binding site sequence of the introduced DNA-molecule;
- G) selection of the identified stem cells by means of the properties of the indicator molecule to an essentially homogeneous population.

In another embodiment of the above method the protein molecule is a transcription factor protein increasing the expression of the gene associated with the change to a specific phenotype.

In a further embodiment of the above method the minimal promoter sequence is arranged in the artificially introduced DNA-molecule between the binding site sequence and the DNA-sequence coding an indicator molecule.

In still another embodiment of the above method the specific stimulus is a physical, chemical or biochemical stimulus.

In yet another embodiment of the above method the properties of the indicator molecule allowing the identification and/or the selection of said indicator molecule are chemical, biochemical or physical properties.

In a further embodiment of the above method the indicator molecule is a cell surface expressed protein, foreign to the native stem cell population.

In another embodiment of the above method the indicator molecule has ferromagnetic properties.

In yet another embodiment of the method the DNA—sequence of the introduced DNA-molecule is a sequence coding an indicator molecule of the following group: green fluorescence protein (GFP), cyan fluorescence protein (CFP) or yellow fluorescence protein (YFP).

In still a further embodiment of the above method the introduced DNA-molecule comprises at least two DNA-sequences, each coding a different indicator molecule.

In another embodiment of the above method at least two introduced DNA-molecules each comprising at least one DNA-sequence coding an indicator molecule are artificially introduced into a plurality of the stem cells of the stem cells sample, whereby the DNA-sequences of the introduced DNA-molecules are coding different indicator molecules.

In still a further embodiment of the above method the different indicator molecules have different properties.

In yet another embodiment of the method for obtaining a homogenous stem cell population of the unmodified stem cells being committed to differentiate to a specific phenotype of stem cells by means of a specific interaction between the cellular DNA and the protein molecule comprising the following additional steps:
- identification of daughter stem cells containing the introduced DNA-molecule after the cell division by means of identification of the presence of the indicator molecule by means of its properties;
- selection and removal of the identified daughter stem cells from the population.

In a further embodiment of the invention the heterogeneous population of stem cells comprises stem cells committed to differentiate to at least two different specific phenotype of stem cells whereby each of the stem cells comprises:
- A) a cellular DNA comprising a plurality of sequences coding different genes and promoters allowing DNA-protein-interactions; and
- B) at least two different DNA-molecules artificially introduced into a plurality of cells of the stem cells sample,
  whereby each of the introduced DNA-molecules comprises
    at least one binding site sequence being apt to interact with the protein molecule;
    at least one DNA-sequence coding an indicator molecule having properties allowing the identification of said indicator molecule; and
    at least one minimal promoter sequence, allowing the gene expression of the indicator molecule; whereby
  the different introduced DNA-molecules comprise two different DNA-sequences coding two different indicator molecules;
  and
- C) at least one indicator molecule having properties allowing the identification of said indicator molecule produced by synthesis of the DNA-sequence of the introduced DNA-molecule, whereby
- D) the stem cells committed to differentiate to the same specific phenotype of stem cells comprises the same indicator molecules.

In still another embodiment the invention comprises two different populations of stem cells comprising stem cells committed to differentiate to at least two different specific phenotype of stem cells whereby each of the stem cells comprises:
- A) a cellular DNA comprising a plurality of sequences coding different genes and promoters allowing DNA-protein-interactions; and
- B) at least one DNA-molecule, each artificially introduced into a plurality of cells of the stem cells sample,
  whereby each of the introduced DNA-molecules comprises
    at least one binding site sequence being apt to interact with the protein molecule;
    at least one DNA-sequence coding an indicator molecule having properties allowing the identification of said indicator molecule; and
    at least one minimal promoter sequence, allowing the gene expression of the indicator molecule; whereby
  the different introduced DNA-molecules comprise two different DNA-sequences coding two different indicator molecules;

and

C) at least one indicator molecule having properties allowing the identification of said indicator molecule produced by synthesis of the DNA-sequence of the introduced DNA-molecule, whereby D) the stem cells committed to differentiate to the same specific phenotype of stem cells comprises the same indicator molecules.

In another embodiment of the two different populations of stem cells at least one DNA-molecule each is artificially introduced under step B) to all stem cells of the stem cells sample.

In still a further embodiment of the above population the different indicator molecules have different properties.

The invention and additional configurations of the invention are explained in even more detail with reference to the partially schematic illustrations of several embodiments.

DETAILED DESCRIPTION OF THE INVENTION

Figure 1:
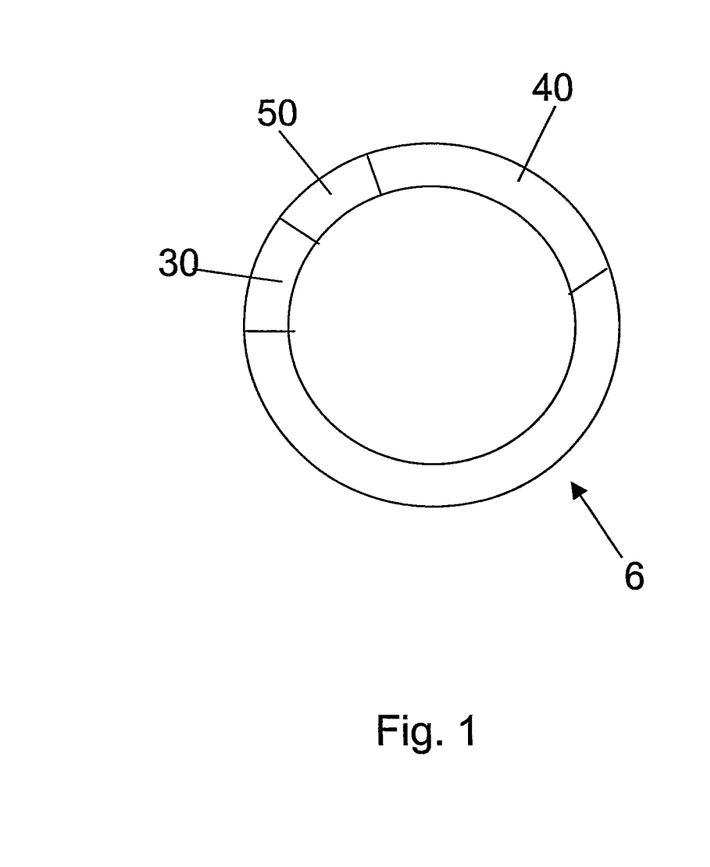
FIG. 1 schematically illustrates the DNA-molecule to be artificially introduced into a stem cell.

FIG. 1 schematically illustrates the DNA-molecule 6 which is to be artificially introduced into a stem cell, whereby this DNA-molecule 6 is in the form of a plasmid and comprises a binding site sequence 30 being able to interact with a specific protein molecule 3, a minimal promoter sequence 50 allowing a gene expression and a DNA-sequence 40 coding an indicator molecule 5 (not shown in FIG. 1). The binding site sequence 30 is a specific sequence being able to interact with a specific protein molecule 3 only and therefore should be selected depending on phenotype of the stem cell the presence of which is desired (the dependencies of cells phenotype and binding site sequences are given below). The minimal promoter sequence 50 is the smallest piece of promoter sequence and allows the gene coded by the DNA-sequence 40 coding an indicator molecule 5 to be expressed. By the presence of a protein molecule 3 which has the property to interact with the binding site sequence 30, protein molecule 3 binds to the binding sequence site 30, so that the expression of the DNA-sequence 40 coding an indicator molecule 5 will be initiated by the minimal promoter sequence 50 and the indicator molecule 5 will be synthesized. In case that the protein molecule 3 does not interact with the binding site sequence 30 (case which might occur only if the protein molecule 3 being able to interact with the binding site sequence 30 of the introduced DNA-molecule 6 is not present in the stem cell) the DNA-sequence 40 coding an indicator molecule 5 cannot be expressed so that the indicator molecule will not be synthesized, so that the presence of the protein molecule 3 in the stem cell is confirmed by the presence of the indicator molecule 5 in the stem cell.

Instead of one binding site sequence 30, one minimal promoter sequence 50 and one DNA-sequence 40 coding an indicator molecule the introduced DNA-molecule 6 might comprise e.g. additional DNA-sequences 30 coding an other indicator molecule 5 or additional binding site sequences (30) enhancing the gene expression.

Figure 2:
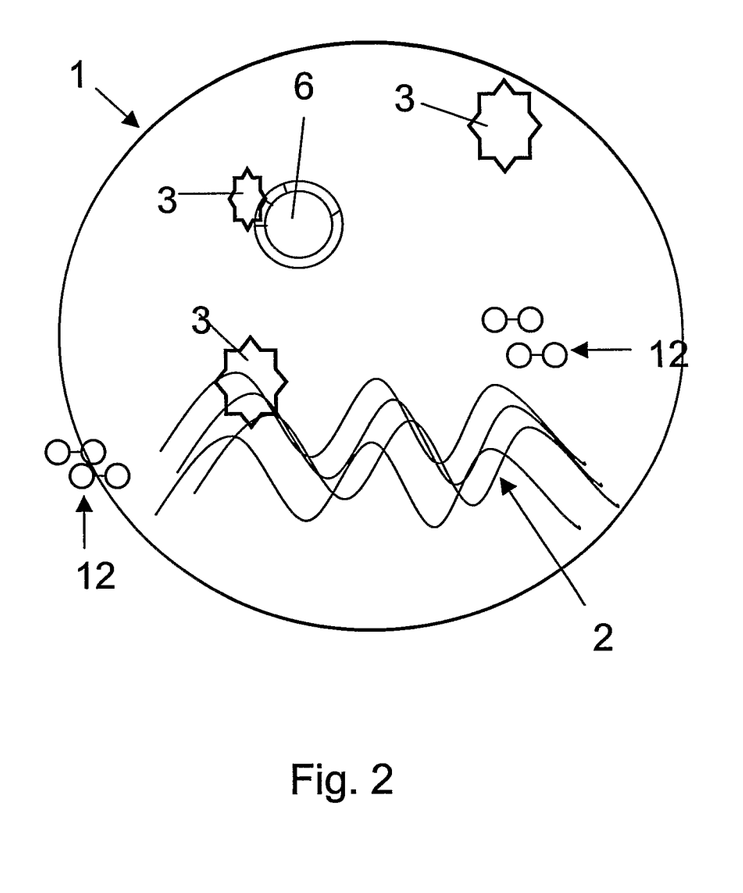
FIG. 2 schematically illustrates the process passing into a stem cell for producing a stem cell according to the invention.

FIG. 2 shows a stem cell 1 comprising a cellular DNA 2 and an artificially introduced DNA-molecule 6 comprising a binding site sequence 30, a minimal promoter sequence 50 and DNA-sequence 40 coding an indicator molecule 5 (shown in FIGS. 3C+3D) having properties allowing its identification and selection. The artificially introduced DNA-molecule 6 can be introduced into the stem cell 1 by a viral transduction or a non-viral transfection. Using a viral transduction to shuttle the construct into the cells implies that the construct will be inserted into an Adenovirus DNA and the cell will be infected using the Adenovirus conventional method. Alternatively the Adenovirus system could be the associate adenovirus or retro- as well as lentiviruses. Any commercially available non-viral system, such as liposome (e.g. Lipofectamine) or AMAXA technology as well as earlier established methods such as calcium phosphate transfection or electroporation could also be used.

Additionally to its cellular DNA 2 and the artificially introduced DNA-molecule 6 the stem cell 1 further comprises a plurality of protein molecules 3. The presence of the protein molecules 3 in the stem cell 1 is caused by applying a specific stimulus 12 to the stem cell 1.

The stem cell 1 is a multipotent cell that can be induced to produce many cell types. The cell phenotype produced is dependent on the stimulus 12 received by the non-committed stem cell. Once stimulated, the stem cell 1 changes its phenotype by switching off certain genes while switching on others. The protein molecule 3 is an early expressed gene which is specific to only one phenotype of stem cells, so that the presence of the protein molecule 3 is caused by the phenotype of the stem cell and by the applying the specific stimulus 12 to the stem cell 1.

Upon applying the specific stimulus 12, protein molecules 3 are produced, bind to sequences being apt to interact with protein molecules 3 and increase the expression of gene. The protein molecule 3 binds also to the binding site sequence 30, causes by means of said binding the expression of the DNA-sequence 40 coding an indicator molecule 5 and causes synthesis of the indicator molecule 5.

Figure 3A:
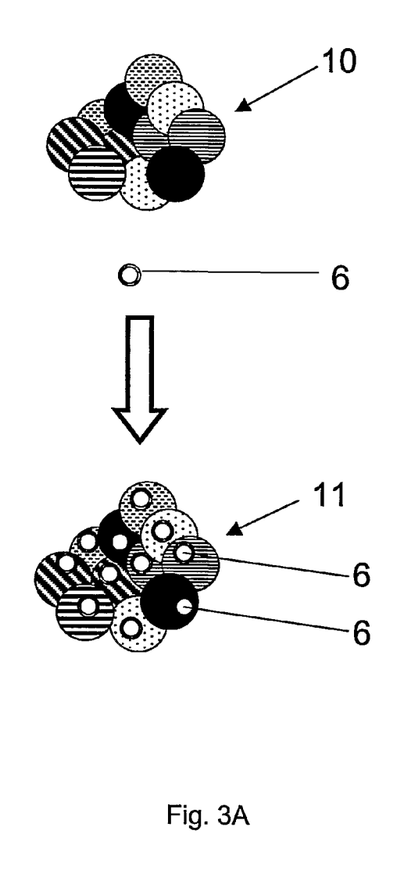
FIG. 3A-3E schematically illustrates the process in vitro according to the inventive method for obtaining an essentially homogeneous population of stem cells being committed to differentiate to the same specific type.

FIG. 3A schematically illustrates a stem cells sample 10 comprising a plurality of stem cells comprising a cellular DNA 2. DNA-molecules 6 each comprising a binding site sequence 30 being apt to interact with a protein molecule 3, a minimal promoter sequence 50 and a DNA-sequence 40 coding an indicator molecule 5 having properties allowing its identification and selection have been artificially introduced to each stem cell of the stem cells sample 10 in order to produce a modified stem cell sample 11.

Figure 3B:
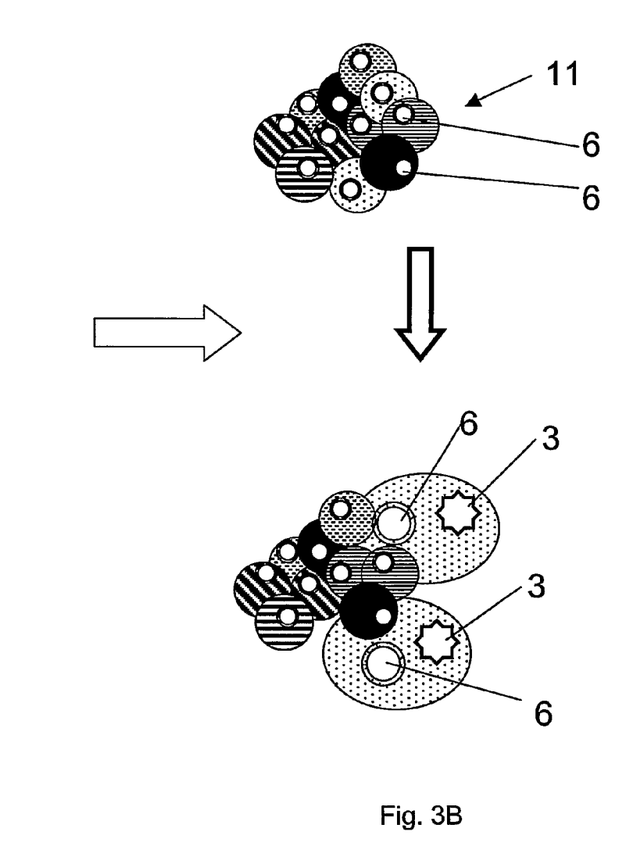

After the artificial introduction of the DNA-molecule 6 in each cell of the stem cell sample 10 a specific stimulus 12 (shown in FIG. 2) has been added to the modified stem cell sample 11. The specific stimulus 12 generating the change of a part of the stem cells of the modified stem cells sample 11 from pluripotent to a specific phenotype of the stem cells has been added to the modified stem cells sample 11. Upon applying the specific stimulus 12 to the modified stem cells sample 11 a part of stem cells has been stimulated to become a specific phenotype of the stem cell corresponding to the specific stimulus 12. These stem cells 1 include also at least one produced protein molecule 3 (FIG. 3B). Due to the specific stimulus 12 the obtained protein molecule 3 is a protein of an early expressed gene and has a function of a transcription factor, i.e. is apt to interact with corresponding specific DNA-sequences.

As a result of the procedure commented above the stem cells sample 10 has been transformed to a modified stem cells sample 11 comprising stem cells each containing an artificially introduced DNA-molecule 6, whereby the modified stem cells sample 11 comprises two groups of stem cells:

Group A: stem cells, which have been stimulated to become a specific phenotype of stem cells, whereby the protein molecule being specific for this phenotype is apt to interact with the binding site sequence 30 of the artificially introduced DNA-molecule 6; and Group B: stem cells, which have not been stimulated to become the specific phenotype (i.e. the protein molecule being specific for this phenotypes is not apt to interact with the binding site sequence 30 of the artificially introduced DNA-molecule 6 as it is not present within the cell).

Figure 3C:
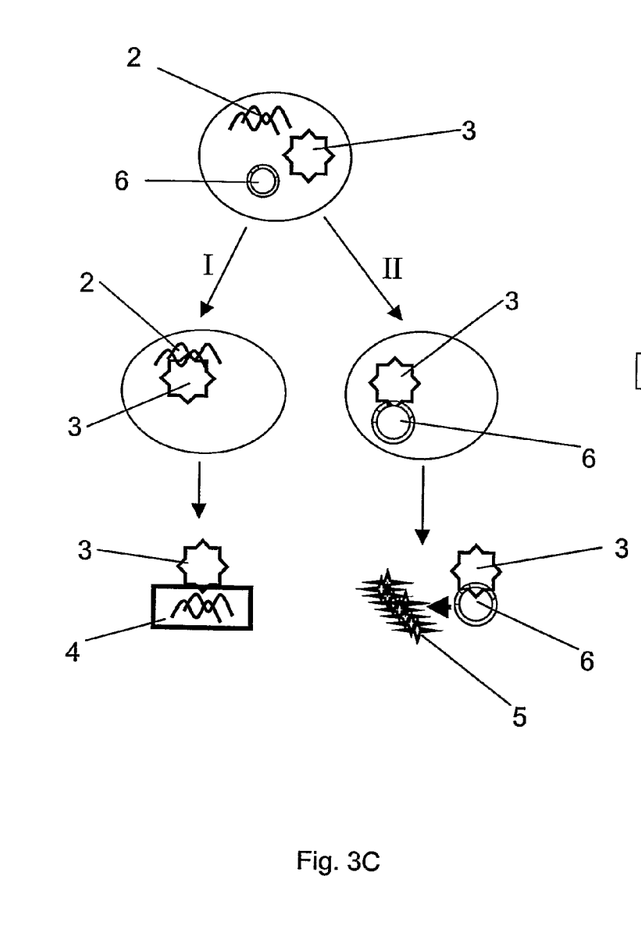
Figure 3D:
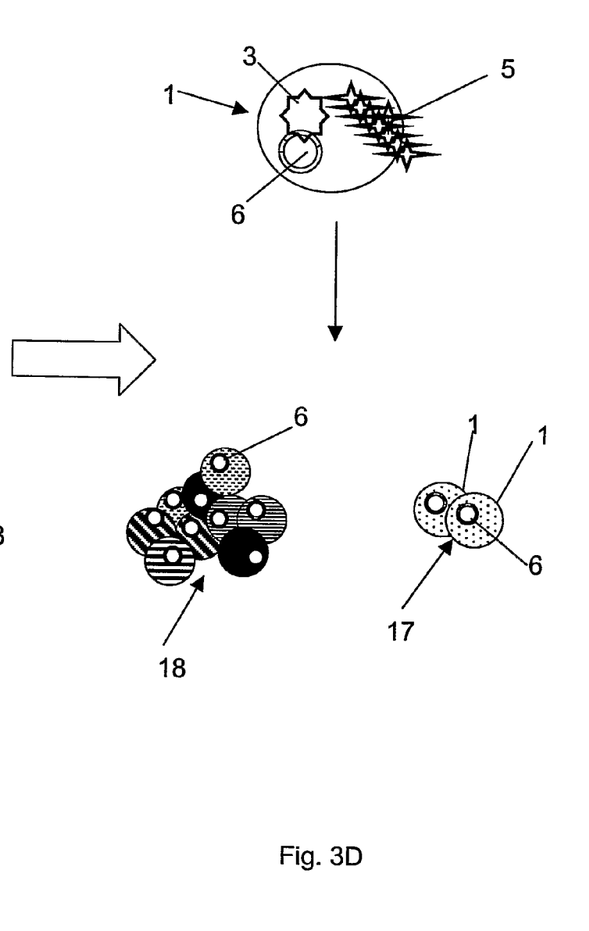

FIG. 3C schematically shows a stem cell 1 of Group A being stimulated by means of specific stimuli 12 to become a specific type and comprising a protein molecule 3, which is apt to interact with a binding site sequence 30 of the artificially introduced DNA-molecule 6.

After the artificial introduction of the DNA-molecule 6 into the stem cell 1 and the stimulation of the stem cell 1 by applying the specific stimulus 12 to the stem cells sample 10 the generated protein molecule 3 interacts with the specific sequences of the cellular DNA 2 in order to increase the natural expression of genes specific for the phenotype of the stem cell 1 on the one hand and with the binding site sequence 30 of the artificially introduced DNA-molecule 6 on the other hand, whereby the binding site sequence 30 is identical to the specific sequences of the cellular DNA 2 interacting with the protein molecule 3 during the natural gene expression.

Due to the interaction between the protein molecule 3 and the cellular DNA 2 the natural gene expression specific to the protein molecule 3 is proceeding. Due to the interaction between the protein molecule 3 and the binding site sequence 30 the expression of the DNA-sequence 40 coding an indicator molecule 5 will be initiated by the minimal promoter sequence 50 and the indicator molecule 5 will be synthesized.

As a result of the procedure illustrated in FIG. 3C the stem cells of group A differ from the stem cells of group B by the presence of the indicator molecule 5, having properties allowing its identification and selection from the stem cell sample 10.

FIG. 3D illustrates the procedure of an identification and separation of the stem cells of the heterogeneous stem cell population to a homogeneous stem cell population 17 comprising exclusively stem cells being committed to differentiate to the same specific phenotype and to the further heterogeneous stem cells population 18 comprising the remaining stem cells. The identification and selection of the target stem cells 1 can be effected by means of any detector device, by means of which the presence of the indicator molecules 5 in the stem cells 1 indicating the specific phenotype of the stem cells 1 can be observed due to the properties of the indicator molecules 5. Examples of few detector devices are mentioned above.

Figure 3E:
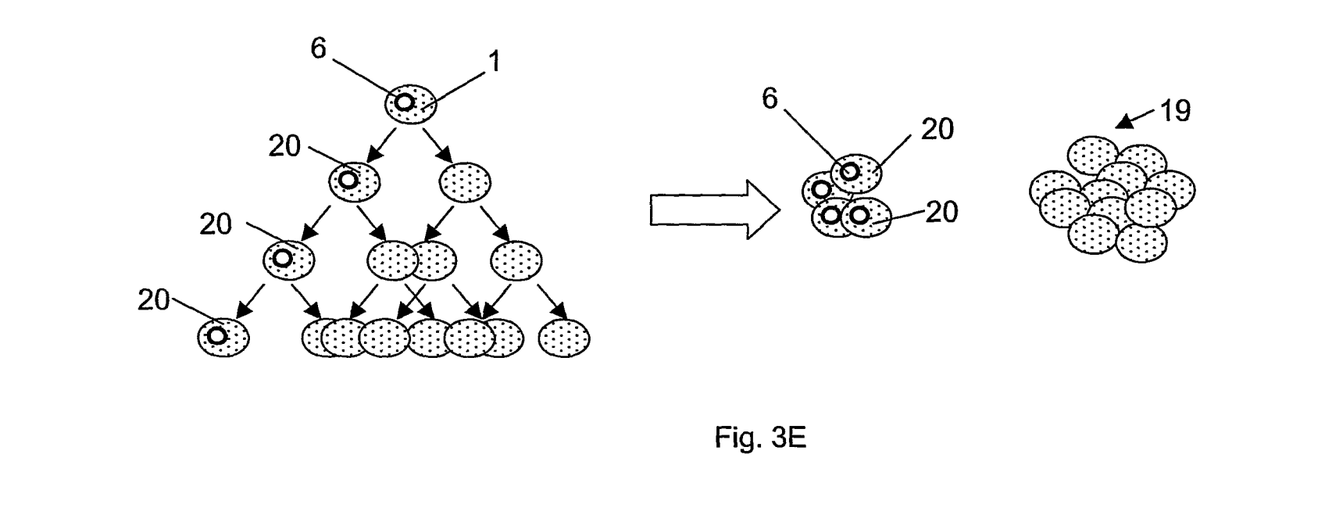

When using adenovirus, or any other non-integrating viral system, the artificially introduced DNA-molecule 6 has been introduced into the stem cells but is not linked to the cellular DNA 2. Therefore the artificially introduced DNA-molecule 6 will not be replicated during the natural cell division, so that only one of the daughter cells of each stem cell 1 will contain the introduced DNA-molecule 6 while the other one will remain unmodified. FIG. 3E illustrates the procedure of the natural cell division of the stem cell 1 of population 17, which produces a population of stem cells comprising a daughter stem cell 20 containing the artificially introduced DNA-molecule 6 and a plurality of unmodified stem cells committed to differentiate to the same specific phenotype. The modified daughter cells (i.e. daughter cell containing the artificially introduced DNA-molecule 6) might be identified and selected according to the identification and selection procedure described above from the homogeneous population 17 of the stem cells in order to obtain a homogeneous unmodified population 19 of the stem cell comprising the unmodified stem cells only.

Analogously, to the procedure presented in the FIGS. 3A-3E any stem cells sample of stem cells can be separated to any number of different homogeneous populations comprising stem cells being committed to differentiate to the same specific phenotype, whereby a number of the DNA-molecules 6 (corresponding to the number of cells phenotypes which are desired to be selected to homogeneous populations) should be prepared so that each DNA-molecule 6 will comprise a binding site sequence 30, a minimal promoter sequence 50 and a DNA-sequence 40 coding an indicator molecule 5, whereby the binding site sequences 30 of each different DNA-molecule 6 should correspond to different cells phenotypes which are desired to be identified and the DNA-sequences 40 coding an indicator molecule 5 of each different DNA-molecule 6 should code sequences of different indicator molecules 5. After the cloning, each kind of the produced DNA-molecules 6 should be artificially introduced to each stem cell of the stem cells. The stem cells sample obtained by the above procedure will comprise a plurality of stem cells 1 committed to differentiate to a number of different specific phenotypes, whereby each phenotype of the cells can be identified by different properties of different indicator molecules 5. Alternatively, the DNA molecule 6 can contain a plurality of binding sequences 30, minimal promoter sequences 50 and DNA-sequences 40 coding indicator molecules 5, arranged in such a way that one DNA-molecule is able to bind different types of protein molecules 3, each protein molecule 3 leading to the production of a particular indicator molecule 5.

For the above mentioned introduction of DNA-sequences the following example for a non-viral transfection is suitable. A mesenchymal stem cell being committed to differentiate to osteoblast has been used as an example; a sequence coding green fluorescence protein (GFP) should be transfected.

The Runx2 DNA reporter construct refers in the following description to the artificially introduced DNA molecule comprising at least:

i) a Runx2 binding site (i.e. sequence influences the interactions between the artificially introduced DNA molecule and Runx2 proteins);

ii) a minimal promoter influencing the initiation of the transcription of the DNA; and iii) a sequence coding green fluorescence molecule (GFP) (i.e. the indicator molecule, which has chemical, physical or biochemical properties allowing identification and selection of said indicator molecule)

A DNA reporter construct, whereby GFP expression is driven by the binding of Runx2 transcription factor protein, is cloned into a plasmid using standard molecular cloning techniques. The exact methods will depend on the plasmid used. The plasmid/reporter construct is precipitated with ethanol, to clean and sterilize the DNA, before being resuspended is a small volume of buffer. Isolated stem cells are plated in 96 well plates, and serial dilutions are created in order to generate wells containing single cell populations. The cells are grown overnight in DMEM medium (Dulbecco/Vogt Modified Eagle's Minimal Essential Medium) containing 10% FCS (Foetal Calf serum) at 37° C. in a 5% $CO_2$ incubator. After 24 hours of growth the DNA is diluted into 3.84 ml of serum free DMEM, briefly vortexed and the liposome reagent is added. The exact values of DNA and liposome need to be optimized for each plasmid and cell type, but common values would be 1 µg of DNA and 10 µl of liposome reagent per ml of serum free medium. The complete medium is aspirated from the cells and they are washed once with serum free medium. Then 40 µl of DNA in serum free medium is added per well. The cells are incubated for 3 hours at 37° C. in a 5% $CO_2$ incubator. Then 200 µl of complete medium is added per well and the cells are grown for a further 16 to 24 hours. The medium is then removed and replaced with 250 µl per well IMDM (Iscove's Modified Dulbecco's Medium), 10% FCS, nonessential aminoacids, 0.1 mM ascorbic acid-2-phosphate and 10 mM β-glycerophosphate with 10 nM dexamethasone (osteogenic medium). The cells will now be continually monitored for green florescence (which indicates the presence of green fluorescent protein and therefore the presence of Runx2).

Single green cells can be isolated and further expanded, leading to a population of cells all of which are destined to become osteoblasts.

The invention and further developments of the invention are explained in more detail in the following application examples.

Example 1

This example explains the procedure for obtaining an essentially homogeneous population of Mesenchymal stem cells according to the invention more precisely and is an illustrative example and should not limit the scope of the invention to this example only. The example refers to a method for obtaining stem cells that will differentiate to osteoblast only, whereby green fluorescence protein (GFP) has been used as the indicator molecule:

Material:
Sterile phosphate buffered saline (PBS), pH 7.2, Ficoll, Methylene Blue.

Culture Medium:
DMEM (Dulbecco/Vogt Modified Eagle's Minimal Essential Medium: powder for 1 L medium, add 0.11 g/L Sodium pyruvate and 3.7 g/L Sodium hydrogencarbonate, 10%(v/v) FCS (Fetal calf serum) Antibiotic/Antimycotic Solution (100×) (liquid, add 1 mL to each 100 mL of medium), T-Flasks 75 $cm^2$/250 mL.

Procedure:
Human bone marrow aspirate obtained from the iliac crest was diluted with 4 mL of DMEM/5% FCS per 1 mL of aspirate. The sample was then centrifuged at 1000 rpm for 5 min. The fat layer and supernatant was removed, and the remaining pellet was resuspended in 4 mL of DMEM/5% FCS.

2.6 mL of room temperature Ficoll per 1 mL of undiluted aspirate was put in 50 mL-Falcon tube and the aspirate/DMEM was pipette very gently on top of the Ficoll. The sample was then centrifuged at 800 g for exactly 20 min at room temperature, acceleration/brake at lowest levels. The mononucleated cells formed an interphase that was collected using a syringe or a pipette. 5 mL of DMEM/5% FCS has been added to each mL of the collected interphase, mixed gently and centrifuged at 400 g for 15 min at room temperature. The supernatant was aspirated and the washing step has been repeated.

The final cell pellet has been resuspended in 10 mL of medium. $4 \times 10^6$ cells per 75 $cm^2$-Flask have been placed in 15 mL culture medium, left at 37° C., 5% $CO_2$, 95% humidity for 2-3 days to let the cells attach to the bottom of the flask.

According to the above procedure isolated mesenchymal stem cells are also considered to represent Mesenchymal stem cells (able to differentiate into osteoblast, chondrocyte, adipocyte, muscle cell, etc, upon addition of the appropriate stimuli).

From the obtained pool of mesenchymal stem cells stem cells which are committed to differentiate into osteoblast only have been isolated by the following procedure:

The Runx2 DNA reporter construct was cloned into the pShuttle vector (Part of the pAdEasy adenoviral construction kit from Statagene) using standard molecular cloning techniques. The pShuttle vector containing the Runx2 driven green fluorescence protein (GFP) reporter was added to bacteria by heat shock transformation. Competent bacteria (bacteria which are receptive to DNA plasmids) XL-10 Gold has been used. One hundred microlitres of chilled bacteria were placed in a 1.5 ml Eppendorf tube and 4 µl of β-mercaptoethanol was added and gently mixed. The cells were then incubated on ice for 10 mins and 0.1-50 ng of the pShuttle vector containing the Runx2 driven GFP reporter is added. The cells were then incubated on ice for 30 mins and then placed in a 42° C. water bath for 30 seconds. After a further 2 min incubation on ice, 0.9 ml of prewarmed (42° C.) NZY+ culture medium (NZY+ is a well known medium for growing bacteria) was added and the tubes were incubated at 37° C. with shaking. The sample was then plated onto Luria Broth agar plates containing kanamycin antibiotic and placed at 37° C. overnight. Only bacteria containing the plasmid will be resistant to the antibiotic and form colonies. After ~36 hours, individual colonies has been picked and grown in overnight in 10 ml LB-kanamycin broth. After 24 hours of growth, the plasmid was then isolated from the bacteria using standard plasmid miniprep techniques.

The isolated plasmid was then linearised with PmeI restriction enzyme, repurified and then treated with alkaline phosphatise for 30 min at 37° C. The linearised, dephosphorylated plasmid was then purified by agarose gel electrophoresis and resuspended in sterile $dH_2O$ at a concentration of 1 µg/µl.

To prepare the adenoviral vector, 40 µl of chilled BJ5183 bacteria were placed in a chilled 1.5 ml centrifuge tube. 1 µl (1 µg) of linearised, dephosphorylated Runx2 DNA reporter construct in pShuttle and 1 µl (100 ng/µl) pAdEasy-1 vector (Part of the pAdEasy adenoviral construction kit from Statagene) were added and gently mixed. This mix was transferred to a chilled electroporation cuvette and pulsed once with electricity at the following setting: 200 ohm, 2.5 kV, 25 µF. After electroporation 1 ml of sterile Luria broth was immediately added. The mix was then added to LB-Kanamycin agarose plates and incubated at 37° C. overnight. After ~24 hours of growth, 10 of the smallest colonies on the plate were picked and grown in 5 ml of LB-Kanamycin broth overnight at 37° C. with shaking. The smallest colonies were likely to be those where the Runx2 DNA reporter construct has been transferred from the pShuttle vector into the pAdEAsy vector by recombination. After ~24 hours of growth the recombinant vector (pAdEasy containing the Runx2 DNA reporter construct) was isolated from the bacteria using standard plasmid miniprep techniques. The plasmid was investigated by sequencing and PacI digestion to ensure suitable recombinants have been prepared.

The pAdEasy adenoviral vector containing the Runx2 DNA reporter construct was then transformed into XL-10 gold bacteria as described earlier for pShuttle.

Adenovirus was then produced from the pAdEasy DNA vector containing Runx2 DNA reporter construct using AD-293 mammalian cells. AD-293 cells were plated in 60-mm tissue culture dishes at a concentration of $7\times10^5$ cells per dish and grown in DMEM medium containing 10% FCS. When the cells were 70% confluent they were washed twice with PBS and 4 ml of DMEM containing 25 µm chloroquine and 7% modified bovine serum was added. The cells were incubated for 30 min at 37° C. in a 5% $CO_2$ incubator. While the cells were incubating, resuspend 5 µg of PacI digested recombinant adenovirus vector containing the Runx2 DNA reporter construct to a final volume of 225 µl in $dH_2O$. 25 µl solution I and 250 µl solution 2 from the virapack transfection kit (Stratagene) was added to the 225 µl of DNA suspension. This was gently mixed and incubated at room temperature for 10 mins. Gently mixed DNA suspension was then added to the cells drop wise with gentle swirling of the medium. The cells with DNA were incubated for 3 hours at 37° C. in a $CO_2$ incubator. Medium was removed and gently replaced with 4 ml of medium containing 25 µM chloroquine. The cells were incubated for a further 6 hours at 37° C. in a $CO_2$ incubator, before removing the medium and replacing with normal complete medium.

After 7-10 days the cells appeared swollen. The medium was removed and 0.5 ml PBS was added. The cells were scraped off with a cell scraper and transferred to a 1.7 ml tube. After 4 times freeze—thaw—procedure the cells were centrifuged at 12,000 g for 10 min at room temperature and the supernatant was aliquot. Store the crude viral stocks at −80° C.

Stem cells to be infected with the adenoviral vector were plated out the night before in 96 well plates. Serial dilutions were created in order to generate wells containing single cell populations. On the day of infection the virus was mixed with 40 µl serum free culture medium to a final concentration of 100 MOI per well. The volume added should be the minimal required to just cover the base of the well. The medium was removed from the mesenchymal stem cells and the viral suspension mix was gently added. The viral mix was incubated for 3 hours at 37° C. in a $CO_2$ incubator. 200 µl DMEM medium was added at 37° C. in a $CO_2$ incubator as normal. After 24 hrs the medium was replaced by 250 µl per well IMDM, 10% FCS, nonessential aminoacids, 0.1 mM ascorbic acid-2-phosphate and 10 mM β-glycerophosphate with 10 nM dexamethasone (osteogenic medium). The cells were continually monitored for green florescence (which indicates the presence of green fluorescent protein and therefore the presence of Runx2).

Single green cells were isolated and further expanded, leading to a population of cells all of which are destined to become osteoblasts.

During monolayer expansion the GFP expressing vector is lost. This leaves a population of cells which have not been genetically modified.

If the required phenotype prefers a three dimensional induction e.g. chondrocytes, the mesenchymal stem cells can be seeded at low density in a hydrogel e.g. alginate. Cells identified by the presence of the indicator molecule can then be later isolated from the mixed population within the gel.

Examples 2-5

Alternatively any further homogeneous populations of stem cells committed to differentiate to the same specific phenotype are obtainable by the method described above. The table according to FIG. 4 illustrates a few examples of specific stimuli and decisive additives of these stimuli, which can be used for obtaining populations of stem cells committed to differentiate to a specific phenotype as well as the corresponding transcription factor proteins specific to the phenotypes of the stem cells.

The invention claimed is:

1. A method for obtaining an essentially homogeneous population of unmodified stem cells that are committed to differentiate to the same specific phenotype, the method comprising the steps:

collecting a stem cells sample comprising a plurality of stem cells each including cellular DNA which comprises a plurality of sequences coding different genes and promoters allowing DNA-protein interactions;

artificially introducing at least one DNA molecule into the plurality of stem cells of the stem cells sample thereby producing a modified stem cell sample, wherein the at least one artificially-introduced DNA molecule comprises:

(I) at least one binding site sequence being apt to interact with a transcription factor protein molecule that is an early expressed gene that is only expressed in stem cells that are stimulated to become the specific phenotype associated with the transcription factor protein molecule;

(II) at least one DNA sequence coding an indicator molecule having properties allowing its identification; and (III) at least one minimal promoter sequence allowing for gene expression of the indicator molecule;

wherein the at least one artificially-introduced DNA molecule is not introduced into the cellular DNA of the stem cells and thus is not replicated by cell division, and wherein the artificially-introduced DNA molecule will be existent in only one daughter cell subsequent to division of each stem cell into which the artificially-introduced DNA molecule has been introduced;

applying a specific stimulus to the modified stem cells sample to stimulate the production of the transcription factor protein molecule that is the early expressed gene that is only expressed in stem cells that are stimulated to become the specific phenotype associated with the specific transcription factor protein molecule and which the at least one binding site sequence of the artificially-introduced DNA molecule is apt to interact with in at least one cell of the modified stem cells sample, whereby due to interaction between the produced transcription factor protein molecule and the binding site sequence of the artificially-introduced DNA molecule the expression of the at least one DNA sequence coding the indicator molecule is initiated by the at least one minimal promoter sequence and the indicator molecule is synthesized;

identifying stem cells comprising the produced transcription factor protein molecule by indentifying the presence of the indicator molecule in the stem cells;

separating the identified stem cells from stem cells in which the indicator molecule is not present to obtain an essentially homogeneous population of stem cells comprising the indicator molecule;

allowing the essentially homogeneous population of stem cells comprising the indicator molecule to undergo cell division to produce:

daughter stem cells containing the artificially introduced DNA molecule; and daughter stem cells that do not contain the artificially-introduced DNA molecule;

identifying, subsequent to the cell division step, daughter stem cells containing the artificially-introduced DNA molecule by identifying the presence of the indicator molecule; and selecting and removing the identified daughter stem cells containing the artificially-introduced DNA molecule from the daughter stem cells that do not contain the artificially-introduced DNA molecule to obtain the essentially homogeneous population of unmodified stem cells that are committed to differentiate to the same specific phenotype.

2. The method according to claim 1, wherein the minimal promoter sequence is arranged in the artificially introduced DNA molecule between the binding site sequence and the DNA sequence coding the indicator molecule.

3. The method according to claim 1, wherein the specific stimulus is a physical, chemical or biochemical stimulus.

4. The method according to claim 1, wherein the properties of the indicator molecule allowing the identification and/or the selection of said indicator molecule are chemical, biochemical or physical properties.

5. The method according to claim 1, wherein the indicator molecule is a cell surface expressed protein, which is foreign to a native stem cell population.

* * * * *